United States Patent [19]

Spitzer et al.

[11] 4,314,573

[45] Feb. 9, 1982

[54] PROCESS FOR CONDITIONING HAIR

[76] Inventors: J. George Spitzer, 44 Coconut Row, Palm Beach, Fla. 33480; Dorothea C. Marra, 107 Fernwood Rd., Summit, N.J. 07901; Lloyd I. Osipow, 2 Fifth Ave., New York, N.Y. 10003; Kevin Claffey, 735 E. 17th St., Brooklyn, N.Y. 11230

[21] Appl. No.: 143,226

[22] Filed: Apr. 24, 1980

Related U.S. Application Data

[63] Continuation-in-part of Ser. No. 41,377, May 22, 1979, abandoned.

[51] Int. Cl.$^3$ .......................... A45D 7/06; A61K 7/06
[52] U.S. Cl. .......................................... 132/7; 424/47; 424/70
[58] Field of Search ....................... 132/7; 424/47, 70

[56] References Cited

PUBLICATIONS

Winter, Gesamten der Parfumerie und Kosmetik, 1952, pp. 113, 114, 414 to 416, 420 to 423.
Sagarin, Cosmetics Science & Technology, 1957, pp. 540 to 548, 557 to 560.
Goodman, Cosmetics Dermatology, 1937, pp. 155, 232 to 234, 238, 240, 243.
Wells et al., Cosmetics and the Skin, 1964, pp. 475 to 478.

*Primary Examiner*—Dale R. Ore

[57] ABSTRACT

A process for conditioning hair is provided which comprises applying to the hair an alcohol-soluble fraction of soybean lecithin in solution in a lower alkanol having two or three carbon atoms, thereby lubricating the hair and facilitating combing, and at the same time reducing the accumulation of an electrostatic charge on the hair during combing, and thereby inhibiting fly-away.

6 Claims, No Drawings

PROCESS FOR CONDITIONING HAIR

This application is a continuation-in-part of Ser. No. 41,377 filed May 22, 1979, and now abandoned.

Hair conditioning compositions have been available for a number of years to facilitate combing of the hair. A hair conditioner should function as both a lubricant and as an antistatic agent, so as to make it easier to comb the hair either wet or dry, without knots and tangles, and with a minimum of resistance, so that the hair is not broken or pulled out during combing. When hair is dry, the accumulation of an electrostatic charge on the hair during combing causes the individual hairs to repel each other, referred to as "fly-away", and thus inhibits laydown of the hair in a desired position. A hair conditioner also is supposed to inhibit the accumulation of such electrostatic charges, and thus prevent fly-away. These effects should be obtainable without the hair becoming limp, oily or greasy.

The cream rinses are especially popular as hair conditioning compositions. Application of a cream rinse requires, first, that the hair be shampooed and then rinsed. The cream rinse is then applied, and massaged into the hair, after which the hair is thoroughly rinsed again. The residue, which is not removed in the rinsing, is the hair conditioning agent. Stearyl dimethyl benzyl ammonium chloride and distearyl dimethyl ammonium chloride, both cationic surface-active agents, are the surfactants of choice in such cream rinses, although other fatty alkyl quaternary ammonium surfactants can be used. The quaternary ammonium surfactants are cationic, and are supposed to be attracted to the wet hair because the wet hair carries a negative charge. The long chain fatty alkyl group such as the stearyl group imparts a lubricating effect, while the cationic group inhibits the build-up of an electrostatic charge.

The cream rinses are quite effective hair conditioners, but they have a number of serious limitations. Since the quaternary ammonium, surfactants are cationic, while shampoos are generally based on anionic surfactants, in order to prevent an interaction between residual anionic surface-active agent from the shampoo before application of the cream rinse, the shampoo has to be thoroughly rinsed from the hair. Otherwise, a deposit will result from the reaction of these two surfactants, causing the hair to appear dull and limp. It is also necessary to thoroughly rinse off the cream rinse, or otherwise the hair again will appear dull and limp, and in the next shampooing the residue of cationic surfactant may react with anionic surfactant present in the shampoo. The result is that the deposit of anionic/cationic surfactant tends to build up on the hair, imparting a dull, limp appearance.

Lecithin is a well known emollient and lubricant that is widely used in skin creams and lotions, hair products, such as shampoos, brilliantines and hair tonics, and in many other types of cosmetic formulations. Formulations indicated for such uses are found in *Cosmetic Science and Technology*, Edward Sagarin et al (1957), as well as in Kirk-Othmer *Encyclopedia of Chemical Technology*, Second Edition, Volume 12, page 357 (1967), both Interscience Publishers, New York. Lecithin is essentially insoluble in water, but is readily dispersed in water. Aqueous lecithin-containing dispersions when applied to the hair function as hair conditioners, serving as lubricants, facilitating wet and dry combing, and also behave as antistatic agents. However, aqueous lecithin dispersions are not practical for use as hair conditioners, because they cannot be used in the manner of a cream rinse, since the lecithin will not remain on the hair, but will be rinsed off. If applied as an aqueous spray after towel-drying the hair, the composition makes the hair wet, and the drying time is rather long.

Kirk-Othmer notes in Table 4, page 353, of Volume 12, that soybean lecithin can be separated into alcohol-soluble and alcohol-insoluble fractions having the following composition:

TABLE 4

Analysis of Lecithin Fractions

| | Oil-free natural lecithin | Alcohol-soluble lecithin | Alcohol-insoluble lecithin |
| --- | --- | --- | --- |
| typical composition, % | | | |
| chemical lecithin | 29.5 | 60 | 4 |
| chemical cephalin | 29.5 | 30 | 28.5 |
| inositol phosphatides | 31.6 | 2.2 | 55 |
| soybean oil | 3.1 | 4 | 4 |
| miscellaneous | 6.3 | 3.8 | 8.5 |
| appearance | granular | soft, waxy solid | granular |
| color | tan | dark tan to brown | yellow to light tan |
| solubility | | | |
| oil | soluble | soluble | soluble |
| water | dispersible | dispersible | dispersible |
| alcohol (warm) | dispersible | soluble | insoluble |
| taste odor | refining procedures yield improvements over natural lecithin; these have proved important in some bland food products | | |
| compatibility | ease of incorporation into an emulsion system is influenced by proper selection of carrier | | |
| emulsion type favored | either oil-in-water or water-in-oil | oil-in-water | water-in-oil |

The alcohol-soluble soybean lecithin fraction is obtained by subjecting so-called "oil-free" natural lecithin to alcohol extraction. The alcohol-soluble fraction is dissolved in the alcohol, and the insoluble residue is the alcohol-insoluble fraction. The fractionated lecithins are sold as such, or diluted with vegetable oils or other liquid carriers in order to form fluid products which are more easily handled.

It is also possible to extract commercial lecithin without first removing the oil, obtaining an oil solution of the alcohol-soluble material.

The term "lecithin" is broadly applied to a disparate variety of materials and therefore subject to misunderstanding. It is used to refer to the phosphatidyl choline fraction of whole lecithin. This fraction is often called "chemical lecithin", and is not a pure compound but a a mixture of phosphatides of various saturated and unsaturated fatty acids. So-called "whole lecithin" also contains cephalin, inositol phosphatides, and other ingredients. The composition of whole lecithin depends upon the source of the lecithin, and on the extent to which it has been refined. Of course, the properties of whole lecithin or lecithin fraction depend on its composition.

In the United States, as acknowledged by Kirk-Othmer in Table 4 above, the lecithin that is commercially available is derived from soybeans. The alcohol-soluble soybean lecithin fraction that is used in the present invention is the alcohol-soluble fraction of so-called "oil free" natural lecithin derived from soybeans, the composition of which is shown in the Kirk-Othmer Table 4 under the heading "Alcohol-Soluble Lecithin". The term "oil-free" is a misnomer, since natural soybean lecithin contains about 3.4% soybean oil, while the alcohol-soluble fraction contains about 4% soybean oil. In the process of the invention, alcohol-soluble soybean lecithin can be used that contains from none up to about 20% soybean oil.

The alcohol-soluble soybean lecithin fraction is water-dispersible, and readily forms oil-in-water emulsions with fats and oils, while the alcohol-insoluble soybean lecithin fraction, rich in the hydrophobic inositol phosphatides, forms water-in-oil emulsions with fats and oils.

In accordance with the invention, it has now been determined that application to hair of a lower alkanol solution of the alcohol-soluble fraction of soybean lecithin gives a remarkably acceptable hair conditioning effect, providing lubricity and an antistatic effect without any of the complications of the cream rinses or lecithin itself. After application of the compositions of the invention, the hair can be combed wet or dry without knots or tangles and without fly-away. The hair feels soft and looks glossy, and neither looks nor feels limp, oily or greasy.

It has been found that the alcohol-soluble fraction of soybean lecithin is compatible with shampoos, and thus poses no cumulative deposit problem as do the cream rinses. Since it is readily dispersible in water, it is easily washed off the hair, and consequently there is no problem of a build-up of film or deposits on the hair, imparting a dull, limp appearance to the hair.

The composition is readily applied by first shampooing, rinsing and towel-drying the hair, and then applying the lower alkanol solution of the alcohol soluble soybean lecithin fraction. The hair can then be combed and possibly set with or without other treatment or processing.

The use of a lower alkanol solution gives fast drying, which is quite important. Hair that has been washed and is still wet or damp is swollen, consequently weakened, and therefore more easily damaged. The alkanol however extracts water from the hair, thus reducing or eliminating the swelling, and toughening the hair.

Moreover, a lower alkanol solution can be applied as a spray, either with the use of a pump or as a propellant-based aerosol spray, giving an easily spreadable composition when applied to the hair, and providing a more uniform coating on the hair than does an aqueous dispersion.

In addition to these advantages, several unusual and unpredictable advantages have been noted. A lower alkanol solution of the alcohol-soluble fraction of soybean lecithin is very much superior to an aqueous dispersion of whole soybeam lecithin in improving wet combing. The treated hair offers much less resistance to combing than hair treated with an aqueous dispersion of whole soybean lecithin. Combing of wet hair treated with the aqueous whole soybean lecithin dispersion is noisy, while the combing of wet hair treated with an alkanol solution of the alcohol-soluble fraction of soybean lecithin of the invention is quiet. Noisy combing is associated with friction and resistance, and indicates that there is appreciably less friction and resistance when a lower alkanol solution of an alcohol-soluble fraction of soybean lecithin is used.

These effects are not due to the alkanol alone. Wet hair swatches treated with alkanol alone also display considerable resistance to combing, and noise.

Hair swatches conditioned with lower alkanol solutions of alcohol-soluble soybean lecithin fraction in accordance with the invention also display better control than hair swatches treated with aqueous dispersions of whole soybean lecithin or alcohol-soluble soybean lecithin fraction. The treated hair swatches of each type were wound on curlers, and allowed to air-dry overnight at room temperature. The swatches were then removed from the curlers and suspended in a chamber at about 60% relative humidity. After several hours the swatches treated with the aqueous dispersions had lost their curls, while those treated with the alkanol solution of the alcohol-soluble fraction of soybean lecithin still retained firm curls.

It is surprising that these results are not obtained if an aqueous dispersion of the alcohol-soluble fraction of soybean lecithin is applied instead of an alkanol solution. It thus appears that to obtain a good hair conditioning effect it is necessary that the lecithin be applied in solution in a lower alkanol.

The lower alkanol employed in the compositions of the instant invention preferably has two or three carbon atoms, including ethanol, n-propanol and isopropanol, and any mixtures of two or all three. These alcohols dry rapidly, extract water from wet swollen hair, are essentially nontoxic, and will dissolve more than 10% by weight of the alcohol-soluble fraction of soybean lecithin, so that alkanol solutions of a wide range of concentrations can be prepared including concentrates that are to be diluted with alkanol or water before use.

It is not necessary that the alkanol solutions of the alcohol-soluble fraction of soybean lecithin that are applied to hair in accordance with the invention contain large amounts of the fraction. Such solutions containing an amount within the range from about 0.3 to about 3% of the alcohol-soluble fraction of soybean lecithin give an excellent conditioning effect. However, for rapid drying, the solvent vehicle should comprise at least 39% by weight of the alkanol. While alkanol alone is quite sufficient as the vehicle, there can also be added other liquid carriers, such as water, as well as the usual adjuncts of hair conditioning compositions, such as perfumes and coloring agents. Propellants may be added if a propellant spray type of composition is desired.

The propellant sprays are of course packaged in pressurized aerosol containers. Any propellant can be used, including fluorocarbons, such as trichlorofluoromethane, dichlorodifluoromethane, chlorodifluoromethane, dichlorofluoromethane, 1,2-dichlorotetrafluoroethane, 1-chloro-1,1-difluoroethane and 1,1-difluoroethane, as well as the hydrocarbons, including n-butane, isobutane and propane, taken singly or in any admixture of hydrocarbons of fluorocarbons and mixtures of hydrocarbons and fluorocarbons.

The above propellants are liquefied in the pressurized container which upon opening of the valve and release of pressure are volatilized and so propel the composition through the dispensing orifice of the container, and dispense a selected quantity of composition as a well-dispersed spray.

Also useful spray propellants are compressed gases, such as nitrous oxide, carbon dioxide and nitrogen.

The compositions of the invention can also be formulated as pump sprays, which are dispensed from pump-type containers. Tonics and lotions are also effective, and can be massaged or rubbed into the hair with the fingers, although it is more difficult with these than with a spray to obtain a uniform distribution of a small amount of the hair conditioning composition on the hair, so that the application may be of wastefully larger amounts.

Accordingly, the alkanol solutions of alcohol-soluble soybean lecithin fraction in accordance with the invention can be broadly formulated as follows:

|  | Parts By Weight | |
| --- | --- | --- |
|  | Overall | Preferred |
| Alcohol-soluble fraction of soybean lecithin | 0.3 to 3 | 0.3 to 2 |
| Alkanol | 37 to 99.7 | 37 to 99.7 |
| Water | 0 to 30 | 0 to 25 |
| Propellant | 0 tp 62.7 | 0 to 50 |
| Water:Alcohol ratio | from 0:1 to 0.4:1 | 0:1 to 0.33:1 |
| Adjunct(s) | 0 to 2 | 0 to 2 |

The alcohol-soluble fraction of soybean lecithin is commercially available. The so-called "oil-free" commercial form containing about 4% soybean oil is preferred, to avoid imparting an oily feel or appearance to the hair, but if this is no disadvantage, of course oil-containing alcohol soluble soybean lecithin fraction containing up to about 20% soybean oil can be used.

If the alcohol-soluble fraction of soybean lecithin is not available, it can easily be prepared simply by extraction of a commercial grade of soybean lecithin, preferably after removing the soybean oil. The extraction can be at room or elevated temperature, with elevated temperature being preferred because of the greater yield of alcohol-soluble fraction that is obtained. The maximum temperature will normally be the boiling point of the alcohol, unless the application of pressure during the extraction is practical.

The alcohol-insoluble residue that remains can be separated be decantation, filtration or centrifuging. The alkanol solution (which is the filtrate, centrifugate or supernatant liquor) is then diluted, and formulated, as desired, to give an alkanol solution of the desired concentration of the alcohol-soluble soybean lecithin fraction. The addition of water reduces the concentration of this fraction that can be dissolved in the vehicle.

Clear solutions are advantageous for commercial marketing, and can be obtained by the application of several filtrations, if necessary.

The amount of alkanol solution applied to the hair is sufficient to give the desired conditioning effect. It is extremely difficult to measure the amount of alcohol-soluble fraction of soybean lecithin deposited on the hair, and so it is not practical to attempt to control the application in this way. However, for spray-type, or propellant base compositions, an application of from 2 to 6 seconds duration of compositions having concentrations of the alcohol-soluble fraction within the stated ranges above will give adequate hair conditioning under nearly all circumstances.

The following Examples in the opinion of the inventors represent preferred embodiments of the invention.

EXAMPLE 1

The "oil-free" alcohol-soluble fraction of soybean lecithin, as obtained by extracting commercially available granular lecithin with ahydrous ethanol, in an amount of one part by weight was dissolved in 99 parts by weight of ethanol. This composition was packaged in a polypropylene bottle fitted with a mechanical spray pump for application of the composition to the hair as a pump spray.

EXAMPLE 2

The alcohol soluble fraction of soybean lecithin, obtained as described in Example 1, one part by weight, was dissolved in 59.0 parts by weight of ethanol, placed in an aerosol container fitted with a conventional aerosol spray valve and button actuator, and then pressurized with 32 parts by weight of isobutane and 8 parts by weight of propane. This composition can then be dispensed as an aerosol spray from the container.

The hair conditioning effectiveness of the composition of Example 1 was evaluated in comparison with two controls.

Control A contained one part of the alcohol-soluble fraction of soybean lecithin dispersed in a vehicle composed of 9 parts by weight of alcohol and 90 parts by weight of water. The amount of alcohol was insufficient in proportion to the water to dissolve any significant amount of the lecithin fraction.

Control B contained one part of commercial whole soybean lecithin (not separated into alcohol-soluble and alcohol-insoluble fractions) dispersed in 99 parts of water.

Comparative tests were conducted using hair swatches that had been bleached blonde. The swatches weighed 1.5 grams, and were 120 mm long below the tie holding the swatch together.

The hair swatches were shampooed twice and rinsed thoroughly after each shampoo, using a shampoo composition containing sodium lauryl sulfate as the anionic surfactant. The swatches were then towel-dried, sprayed with the text composition using a spray pump until thoroughly saturated, and then wrapped on hair rollers 12.5 mm in diameter, using minimum tension during winding. The rollers were secured with snap clips, and the wound hair swatches were allowed to dry overnight. The swatches were then hung on a rack in a closed humidity chamber at various relative humidities. The curl length was measured periodically, to determine curl droop. In all instances, the initial curl length was 25 mm.

The following Table I lists the results obtained after measuring the curl length, minutes, hours or days after hanging.

TABLE I

| | Test 1<br>70% RH, 22° C. | Test 2<br>60% RH, 22° C. | | Test 3<br>60% RH, 22° C. | | Test 4<br>80% RH, 20°C. |
|---|---|---|---|---|---|---|
| | 15 min after | 4 hrs after | 6 hrs after | 2 hrs after | 4 hrs after | 3 days after |
| Example | 30 | 25 | 25 | 30 | 40 | 65 |
| Control A | 40 | 60 | 70 | 55 | 60 | 90 |
| Control B | 40 | 60 | 70 | 65 | 80 | 100 |

A further evaluation was carried out of Example 1 and Control B against ethanol and water using hair swatches as described above which were towel-dried and then sprayed until thoroughly saturated with test solution. Using clean combs, three subjects combed the saturated swatches, and rated them in blind tests. The swatch that gave a minimum resistance was given a rating of 1, the swatch showing a maximum resistance was given a rating of 5, and intermediate resistances were given intermediate ratings. The average results obtained in multiple tests with the three observers were as follows:

TABLE II

| | Resistance to Combing |
|---|---|
| Example 1 | 1 |
| Control B | 3 |
| Control C 100% ethanol | 4 |
| Control D 100% water | 5 |

All swatches gave noisy combing except those saturated with the composition of Example 1.

A further evaluation was carried out using hair swatches that had been bleached blonde, each weighing 3 grams. These were thoroughly shampooed and dried, and then immersed in jars containing the composition of Example 1 and the composition of Control A. In blind tests, seven subjects were asked to comb the swatches while saturated with the compositions, and determine which was easier to comb. All seven subjects selected the swatches that had been treated with the composition of Example 1 as being much easier to comb, i.e., less friction. None of the subjects had any difficulty in distinguishing between the swatches treated with the two compositions. The test was repeated with virgin hair swatches evaluated by the same seven subjects. Again, all seven subjects selected the swatches that had been treated with the composition of Example 1 as being much easier to comb.

Having regard for the foregoing disclosure the following are the inventive and patentable embodiments thereof.

We claim:

1. A process for conditioning hair which comprises applying to the hair an effective hair-conditioning amount of an alcohol-soluble fraction of soybean lecithin in solution in a lower alkanol having two or three carbon atoms, and then combing the hair, the alcohol-soluble lecithin fraction lubricating the hair and facilitating combing, and at the same time reducing the accumulation of an electrostatic charge on the hair during combing, and inhibiting fly away.

2. A process according to claim 1 in which the concentration of alcohol-soluble soybean lecithin fraction in the solution is within the range from about 0.3 to about 3% by weight.

3. A process according to claim 1 in which the alkanol is ethanol.

4. A process according to claim 1 in which the alkanol is n-propanol.

5. A process according to clam 1 in which the alkanol is isopropanol.

6. A process according to claim 1 which comprises spraying the solution on the hair.

* * * * *